United States Patent
McAuley et al.

(10) Patent No.: US 9,295,799 B2
(45) Date of Patent: *Mar. 29, 2016

(54) BREATHING ASSISTANCE APPARATUS

(75) Inventors: Alastair Edwin McAuley, Auckland (NZ); Ivan Milivojevic, Cambridge (GB); Aidan Mark Shotbolt, Dunedin (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 1168 days.

This patent is subject to a terminal disclaimer.

(21) Appl. No.: 10/599,394

(22) PCT Filed: Mar. 30, 2005

(86) PCT No.: PCT/NZ2005/000062
§ 371 (c)(1),
(2), (4) Date: Mar. 27, 2007

(87) PCT Pub. No.: WO2005/094928
PCT Pub. Date: Oct. 13, 2005

(65) Prior Publication Data
US 2007/0267017 A1 Nov. 22, 2007

(30) Foreign Application Priority Data
Apr. 2, 2004 (NZ) .......................... 532108

(51) Int. Cl.
*A61M 16/06* (2006.01)
(52) U.S. Cl.
CPC ........... *A61M 16/06* (2013.01); *A61M 16/0616* (2014.02); *A61M 16/0622* (2014.02); *A61M 16/0633* (2014.02)

(58) Field of Classification Search
CPC ............ A61M 16/06; A61M 2016/06; A61M 2016/0616
USPC ............. 128/206.21, 206.24, 206.25, 206.26, 128/206.28
See application file for complete search history.

(56) References Cited

U.S. PATENT DOCUMENTS

| | | | |
|---|---|---|---|
| 2,228,218 A | 1/1941 | Schwartz | |
| 5,243,971 A | 9/1993 | Sullivan et al. | |
| 5,570,689 A | 11/1996 | Starr et al. | |
| 5,857,460 A | 1/1999 | Popitz | |
| 6,016,804 A | 1/2000 | Gleason et al. | |
| 6,112,746 A | 9/2000 | Kwok et al. | |
| 6,467,483 B1 | 10/2002 | Kopacko et al. | |
| 6,513,526 B2 * | 2/2003 | Kwok et al. | ............. 128/206.24 |

(Continued)

FOREIGN PATENT DOCUMENTS

| | | |
|---|---|---|
| WO | 98/04310 | 2/1998 |
| WO | 00/78384 | 12/2000 |
| WO | 2004/007010 | 1/2004 |

*Primary Examiner* — Justine Yu
*Assistant Examiner* — LaToya M Louis
(74) *Attorney, Agent, or Firm* — Knobbe, Martens, Olson & Bear, LLP.

(57) ABSTRACT

A breathing assistance apparatus is designed for use with delivery of respiratory gases to a patient. The breathing assistance apparatus includes a patient interface, having a body section adapted to cover the nose, or nose and mouth of a patient and a sealing interface. The sealing interface includes at least an outer sealing member. The outer sealing member is adapted to attach to the body section in a sealing manner and has a substantially thin section in at least its nasal bridge region. The thin section is substantially thinner than the rest of the outer sealing member.

27 Claims, 19 Drawing Sheets

(56) References Cited

U.S. PATENT DOCUMENTS

| | | |
|---|---|---|
| 6,631,718 B1 | 10/2003 | Lovell |
| 7,007,696 B2 * | 3/2006 | Palkon et al. ............ 128/207.13 |
| 7,021,311 B2 * | 4/2006 | Gunaratnam et al. ... 128/206.24 |
| 7,290,546 B2 * | 11/2007 | Sprinkle et al. .......... 128/206.24 |
| 7,523,754 B2 * | 4/2009 | Lithgow et al. .......... 128/206.24 |
| 8,567,404 B2 | 10/2013 | Davidson et al. |
| 2001/0020474 A1 * | 9/2001 | Hecker et al. ............ 128/206.28 |
| 2003/0019496 A1 | 1/2003 | Kopacko et al. |
| 2003/0089373 A1 | 5/2003 | Gradon et al. |
| 2004/0182398 A1 | 9/2004 | Sprinkle et al. |
| 2008/0110464 A1 | 5/2008 | Davidson et al. |
| 2015/0090266 A1 | 4/2015 | Melidis et al. |

* cited by examiner

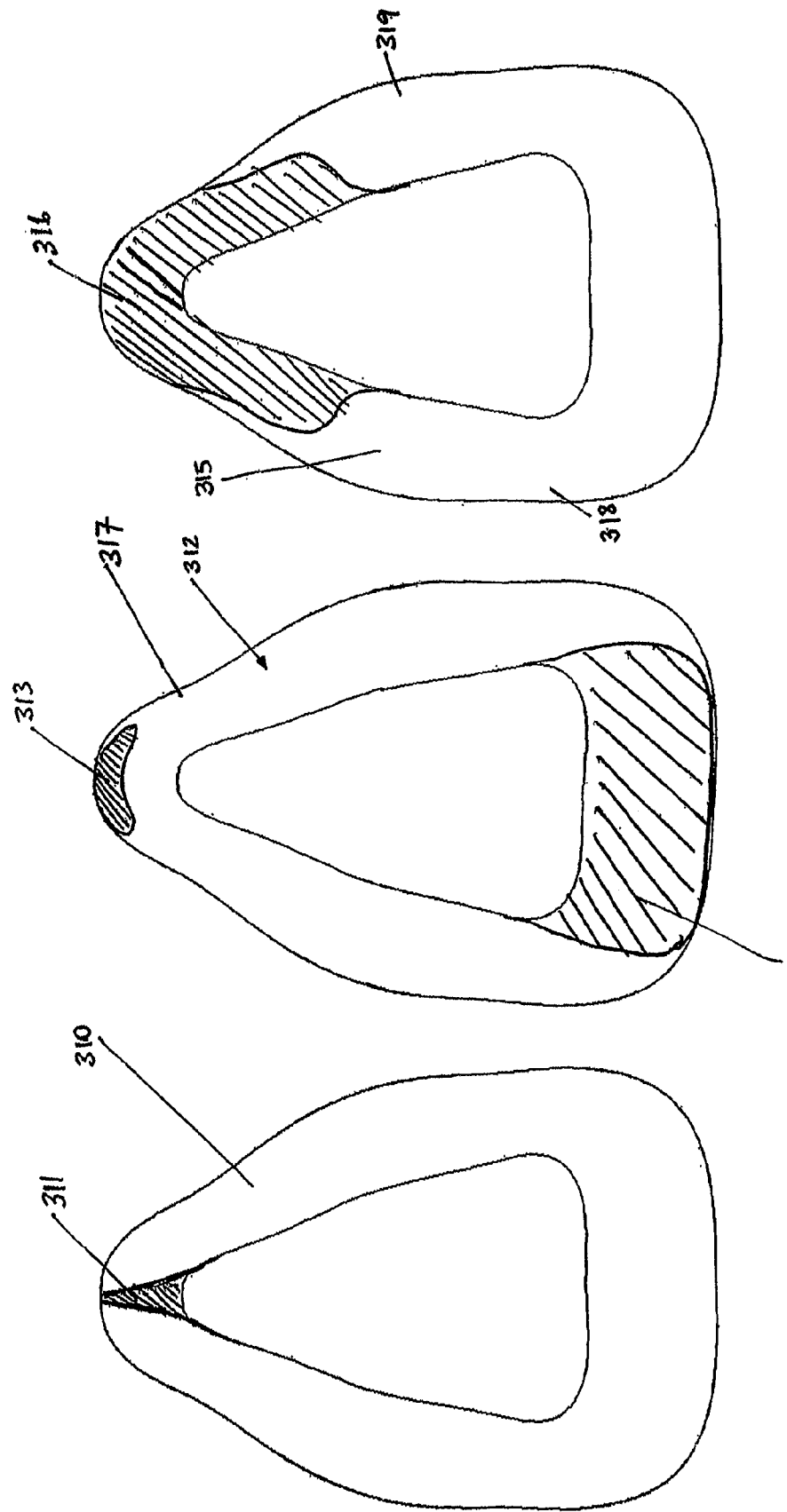

BREATHING ASSISTANCE APPARATUS

This application is a 371 of PCT/NZ2005/000062 filed on Mar. 30, 2005 which claims the foreign priority of New Zealand application No. 532108 filed on Apr. 2, 2004,

BACKGROUND OF THE INVENTION

1. Field of the Invention

This invention relates to patient interfaces particularly though not solely for use in delivering CPAP therapy to patients suffering from obstructive sleep apnoea (OSA).

2. Summary of the Prior Art

In the art of respiration devices, there are well known variety of respiratory masks which cover the nose and/or mouth of a human user in order to provide a continuous seal around the nasal and/or oral areas of the face such that gas may be provided at positive pressure within the mask for consumption by the user. The uses for such masks range from high altitude breathing (i.e., aviation applications) to mining and fire fighting applications, to various medical diagnostic and therapeutic applications.

One requisite of such respiratory masks has been that they provide an effective seal against the user's face to prevent leakage of the gas being supplied. Commonly, in prior mask configurations, a good mask-to-face seal has been attained in many instances only with considerable discomfort for the user. This problem is most crucial in those applications, especially medical applications, which require the user to wear such a mask continuously for hours or perhaps even days. In such situations, the user will not tolerate the mask for long durations and optimum therapeutic or diagnostic objectives thus will not be achieved, or will be achieved with great difficulty and considerable user discomfort.

U.S. Pat. No. 5,243,971 and U.S. Pat. No. 6,112,746 are examples of prior art attempts to improve the mask system U.S. Pat. No. 5,570,689 and PCT publication No. WO 00/78384 are examples of attempts to improve the forehead rest.

Where such masks are used in respiratory therapy, in particular treatment of obstructive sleep apnea (OSA) using continuance positive airway pressure (CPAP) therapy, there is generally provided in the art a vent for washout of the bias flow or expired gases to the atmosphere. Such a vent may be provided for example, as part of the mask, or in the case of some respirators where a further conduit carries the expiratory gases, at the respirator. A further requisite of such masks is the washout of gas from the mask to ensure that carbon dioxide build up does not occur over the range of flow rates. In the typical flow rates in CPAP treatment, usually between 4 cm $H_2O$ to 20 cm $H_2O$, prior art attempts at such vents have resulted in excessive noise causing irritation to the user and any bed partners.

In common with all attempts to improve the fit, sealing and user comfort is the need to avoid a concentrated flow of air at any portion of the respiratory tracts. In particular with oral masks or mouthpieces it is a disadvantage of prior art devices that the oral cavity may become overly dehydrated by use of the device, causing irritation and possible later complications.

Furthermore, a common complaint of a user of CPAP therapy is pressure sores caused by the mask about the nose and face and in particular in the nasal bridge region of the user.

SUMMARY OF THE INVENTION

It is an object of the present invention to attempt to provide a patient interface which goes some way to overcoming the abovementioned disadvantages in the prior art or which will at least provide the industry with a useful choice.

Accordingly in a first aspect the present invention consists in a breathing assistance apparatus, for use with delivery of respiratory gases to a patient comprising:

a patient interface, having a body section adapted to cover the nose, or nose and mouth of said patient, a sealing interface, including at least an outer sealing member, said outer sealing member adapted to attach to said body section in a sealing manner, said outer sealing member having a substantially thin section in at least its nasal bridge region, said thin section being substantially thinner than the rest of said outer sealing member, wherein said outer sealing member is adapted to seal around the facial contours of said patient thereby providing a sealed fluid communication to the respiratory tract of said patient.

The invention consists in the foregoing and also envisages constructions of which the following gives examples.

BRIEF DESCRIPTION OF THE DRAWINGS

Preferred forms of the present invention will now be described with reference to the accompanying drawings.

FIG. 31 is a front view of a first alternative outer sealing member.

FIG. 32 is a front view of a second alternative outer sealing member.

FIG. 33 is a front view of a third alternative outer sealing member.

DETAILED DESCRIPTION OF THE PREFERRED EMBODIMENTS

The sealing interface of the present invention provides improvements in the delivery of CPAP therapy. In particular a patient interface is described which reduces the pressure of the mask on the patient's face and may be quieter for the patient to wear and reduces the side leakage as compared with the prior art. It will be appreciated that the patient interface as described in the preferred embodiment of the present invention can be used in respiratory care generally or with a ventilator, but will now be described below with reference to use in a humidified CPAP system. It will also be appreciated that the present invention can be applied to any form of patient interface including, but not limited to, nasal masks, oral masks and mouthpieces.

Figure 1:
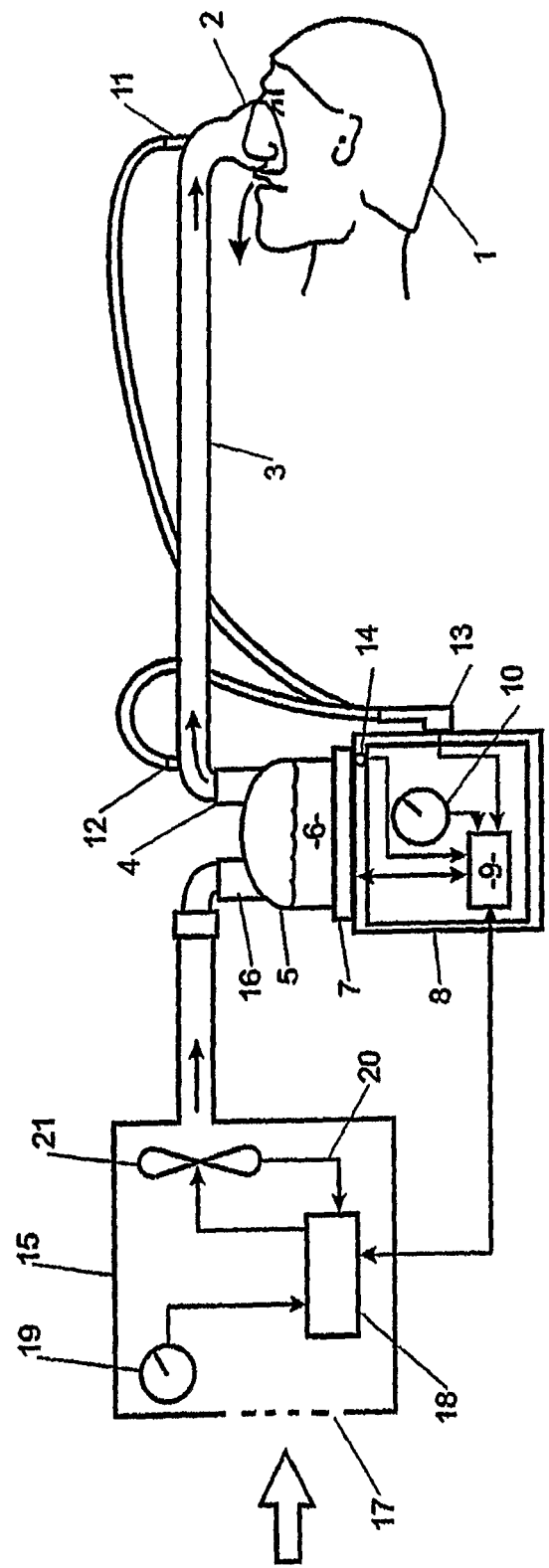
FIG. 1 is a block diagram of a humidified continuous positive airway pressure (system) as might be used in conjunction with the sealing interface of the present invention.

With reference to FIG. 1 a humidified Continuous Positive Airway Pressure (CPAP) system is shown in which a patient 1 is receiving humidified and pressurised gases through a patient interface 2 connected to a humidified gases transportation pathway or inspiratory conduit 3. It should be understood that delivery systems could also be VPAP (Variable Positive Airway Pressure) and BiPAP (Bi-level Positive Airway Pressure) or numerous other forms of respiratory therapy. Inspiratory conduit 3 is connected to the outlet 4 of a humidification chamber 5 that contains a volume of water 6. Inspiratory conduit 3 may contain heating means or heater wires (not shown) which heat the walls of the conduit to reduce condensation of humidified gases within the conduit. Humidification chamber 6 is preferably formed from a plastics material and may have a highly heat conductive base (for example an aluminium base) which is in direct contact with a heater plate 7 of humidifier 8. Humidifier 8 is provided with control means or electronic controller 9 which may comprise a microprocessor based controller executing computer software commands stored in associated memory.

Controller 9 receives input from sources such as user input means or dial 10 through which a user of the device may, for example, set a predetermined required value (preset value) of humidity or temperature of the gases supplied to patient 1. The controller may also receive input from other sources; for example temperature and/or flow velocity sensors 11 and 12 through connector 13 and heater plate temperature sensor 14. In response to the user set humidity or temperature value input via dial 10 and the other inputs, controller 9 determines when (or to what level) to energise heater plate 7 to heat the water 6 within humidification chamber 5. As the volume of water 6 within humidification chamber 5 is heated, water vapor begins to fill the volume of the chamber above the water's surface and is passed out of the humidification chamber 5 outlet 4 with the flow of gases (for example air) provided from a gases supply means or blower 15 which enters the chamber through inlet 16. Exhaled gases from the patient's mouth are passed directly to ambient surroundings in FIG. 1.

Blower 15 is provided with variable pressure regulating means or variable speed fan 21 which draws air or other gases through blower inlet 17. The speed of variable speed fan 21 is controlled by electronic controller 18 (or alternatively the function of controller 18 could carried out by controller 9) in response to inputs from controller 9 and a user set predetermined required value (preset value) of pressure or fan speed via dial 19.

Nasal Mask

Figure 2:
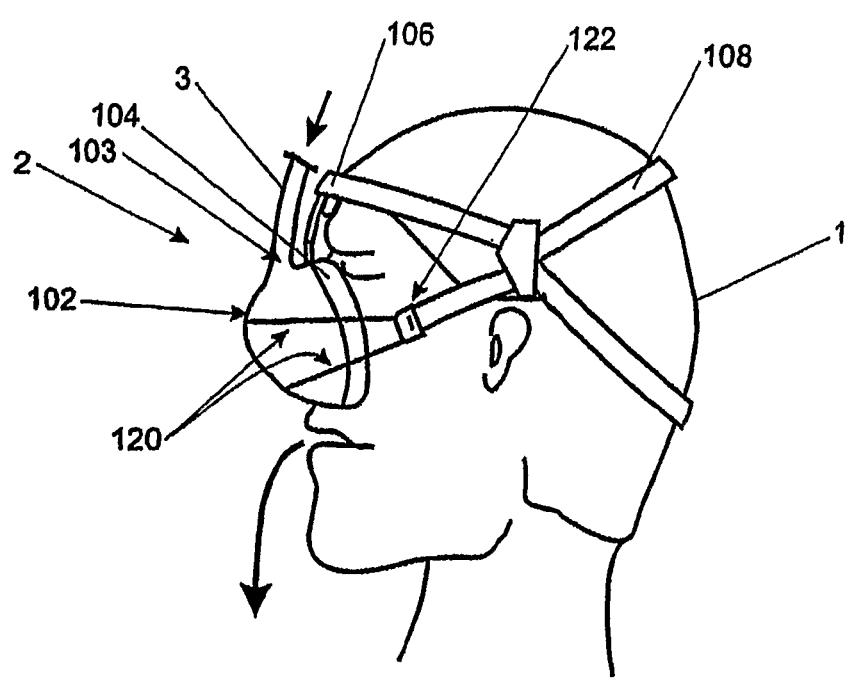
FIG. 2 is an illustration of the nasal mask including a sealing interface in use according to the preferred embodiment of the present invention.

According to a first embodiment of the present invention the patient interface is shown in FIG. 2 as a nasal mask. The mask includes a hollow body 102 with an inlet 103 connected to the inspiratory conduit 3. The mask 2 is positioned around the nose of the patient 1 with the headgear 108 secured around the back of the head of the patient 1. The restraining force from the headgear 108 on the hollow body 102 and the forehead rest 106 ensures enough compressive force on the mask cushion 104, to provide an effective seal against the patient's face.

The hollow body 102 is constructed of a relatively inflexible material for example, polycarbonate plastic. Such a material would provide the requisite rigidity as well as being transparent and a relatively good insulator. The expiratory gases can be expelled through a valve (not shown) in the mask, a further expiratory conduit (not shown), or any other such method as is known in the art.

Mask Cushion

Figure 3:
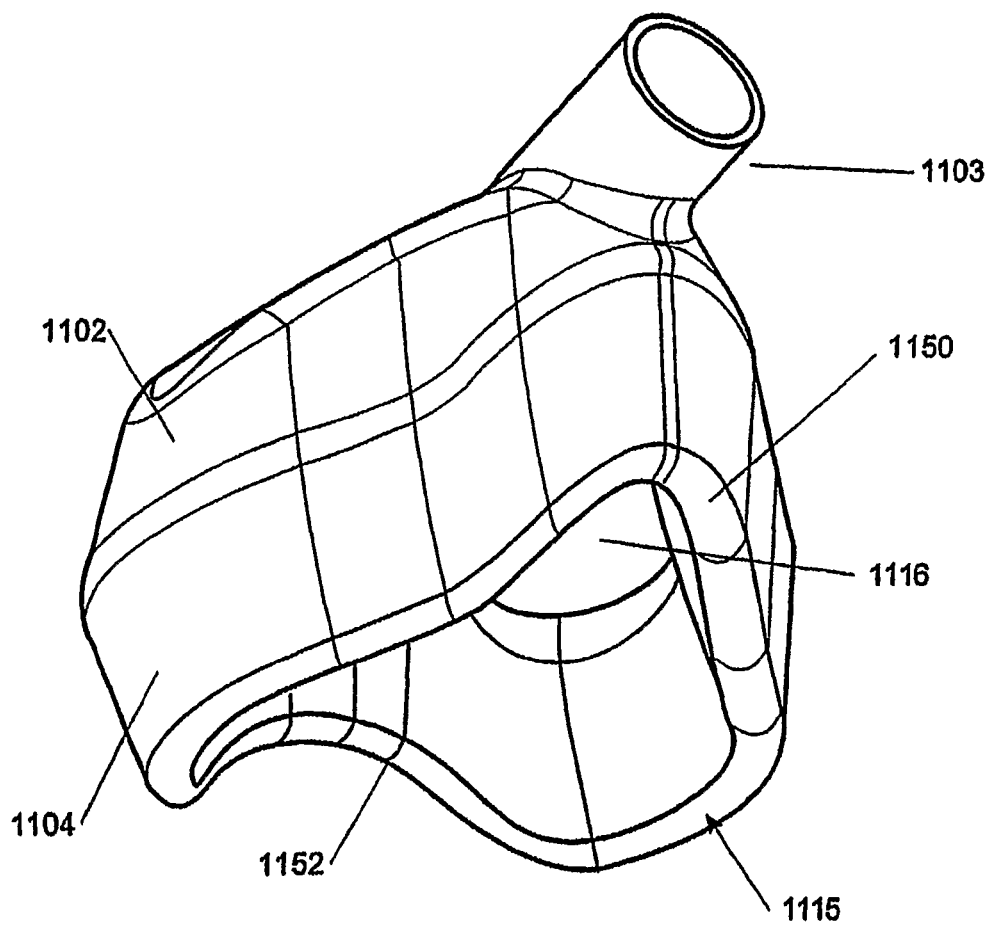
FIG. 3 shows a perspective view of a mask with a sealing interface that is a cushion.
Figure 4:
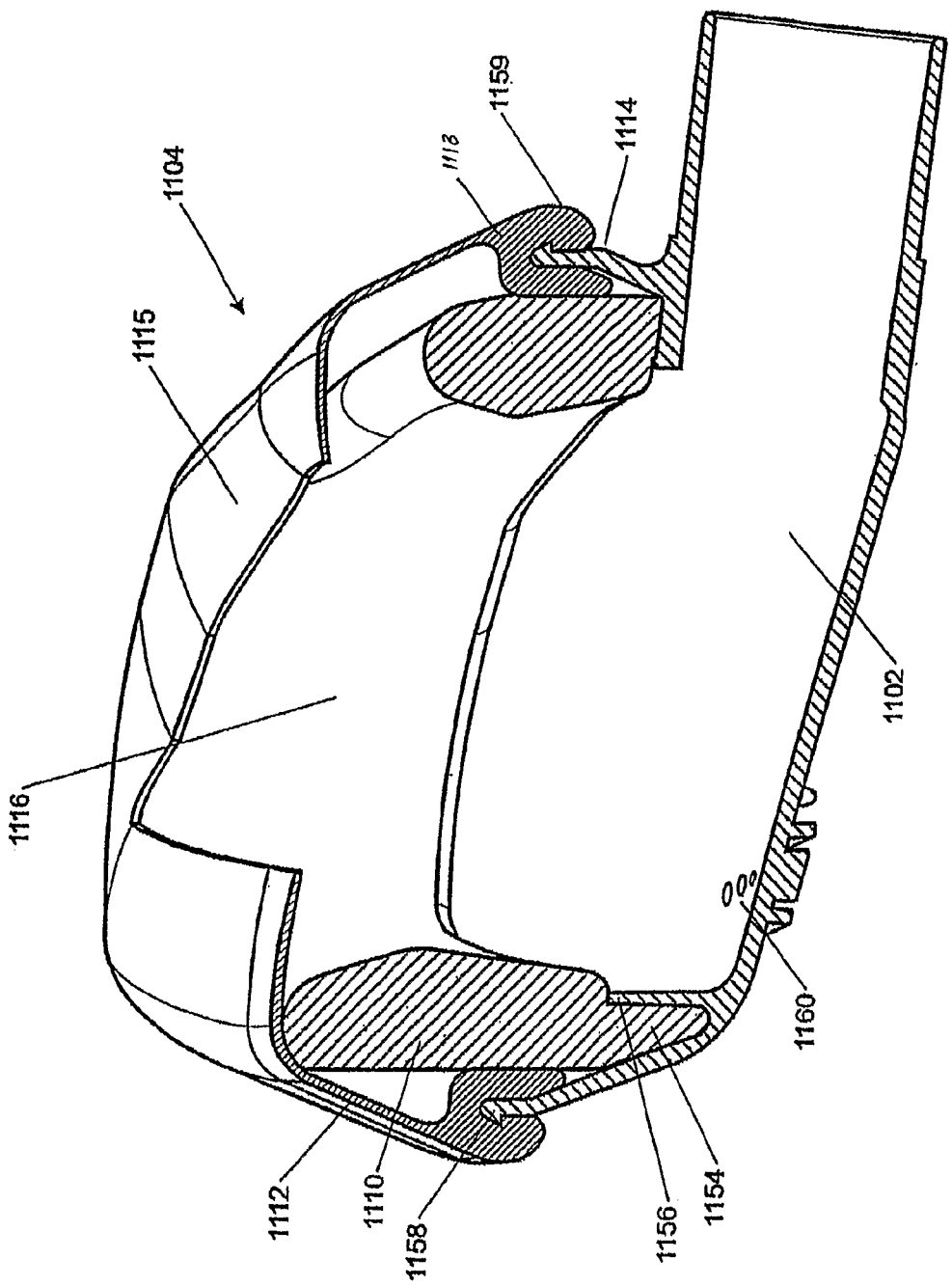
FIG. 4 is a cutaway view of the mask showing the sealing interface cushion that has an inner sealing member and an outer sealing member.
Figure 7:
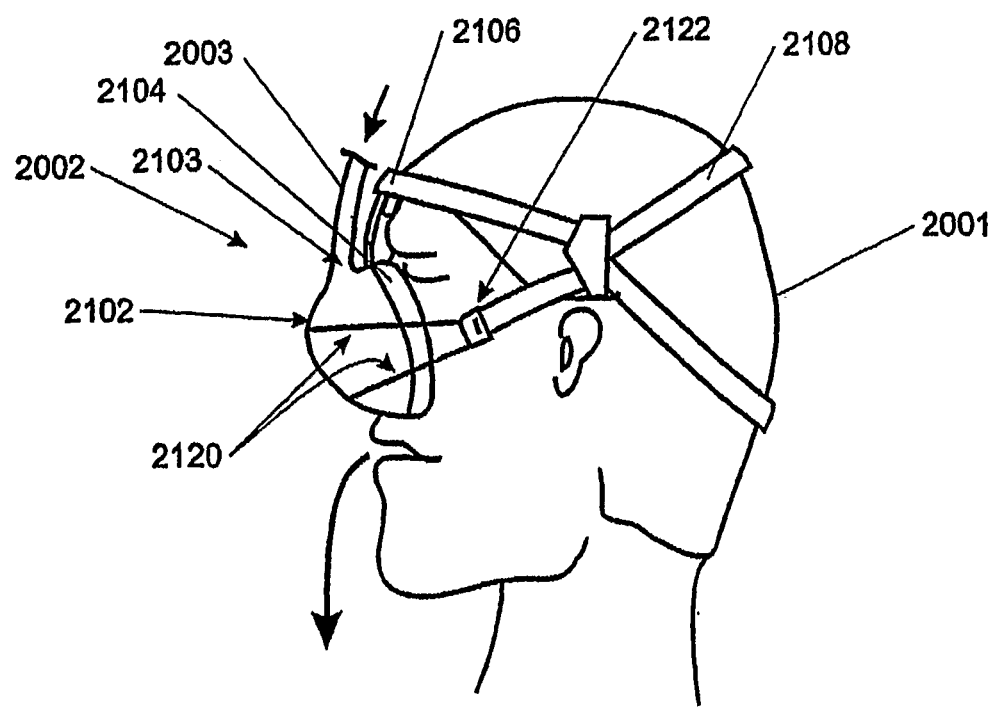
FIG. 7 shows a mask and sealing interface as used with a forehead rest on a patient.

Referring now to FIGS. 3 and 4 in particular, the mask cushion 1104 is provided around the periphery of the nasal mask 1102 to provide an effective seal onto the face of the patient to prevent leakage. The mask cushion 1104 is shaped to approximately follow the contours of a patient's face. The mask cushion 1104 will deform when pressure is applied by the headgear 2108 (see FIG. 7) to adapt to the individual contours of any particular patient. In particular, there is an indented section 1150 intended to fit over the bridge of the patient's nose as well as an indented section 1152 to seal around the section beneath the nose and above the upper lip.

In FIG. 4 we see that the mask cushion 1104 is composed of an inner sealing member that is an inner cushion 1110 covered by an outer sealing sheath or member 1112. The inner cushion 1110 is constructed of a resilient material for example polyurethane foam, to distribute the pressure evenly along the seal around the patient's face. In other forms the inner cushion 1110 may be formed of other appropriate material, such as silicone or other composite materials. The inner cushion 1110 is located around the outer periphery 1114 of the open face 1116 of the hollow body 1102. Similarly the outer sheath 1112 may be commonly attached at its base 1113 to the periphery 1114 and loosely covers over the top of the inner cushion 1110.

Figure 5:
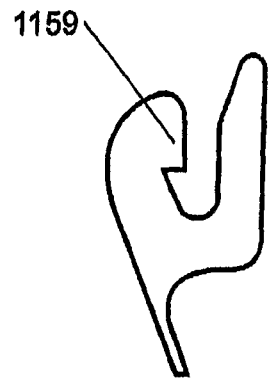
FIG. 5 is a cutaway view of the periphery of the outer sealing member or membrane.
Figure 6:
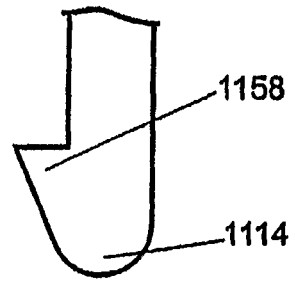
FIG. 6 is a cutaway view of the periphery of the mask body portion.

In the preferred embodiment of the present invention as shown in FIGS. 4 to 6 the bottom of the inner cushion 1110 fits into a generally triangular cavity 1154 in the hollow body 1102. The cavity 1154 is formed from a flange 1156 running mid-way around the interior of the hollow body.

The outer sheath 1112 fits in place over the cushion 1110, holding it in place. The sheath 1112 is secured by a snap-fit to the periphery 1114 of the hollow body. In FIGS. 5 to 6 the periphery 1114 is shown including an outer bead 1158. The sheath 1112 includes a matching bead 1159, whereby once stretched around the periphery; the two beads engage to hold the sheath in place.

Figure 9:
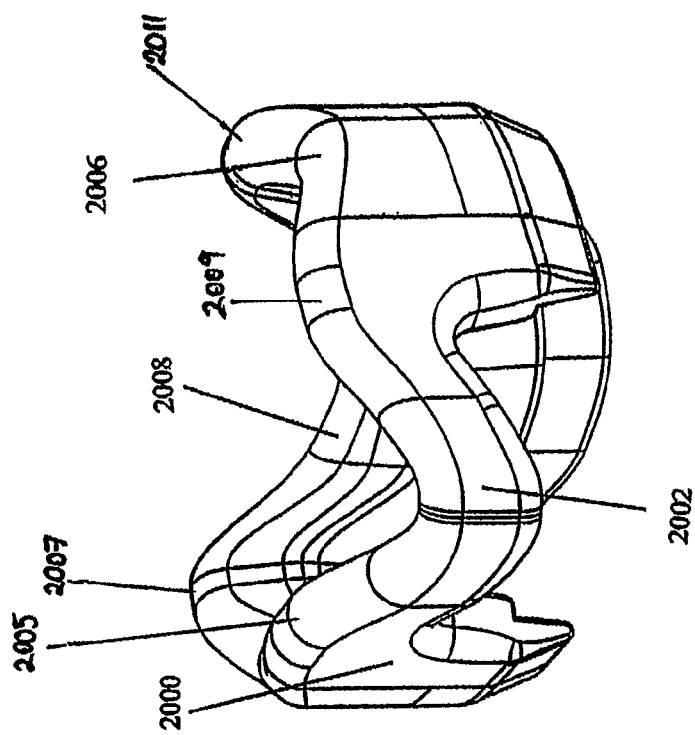
FIG. 9 shows perspective view of an inner sealing member of the second preferred embodiment of the sealing interface.
Figure 8:
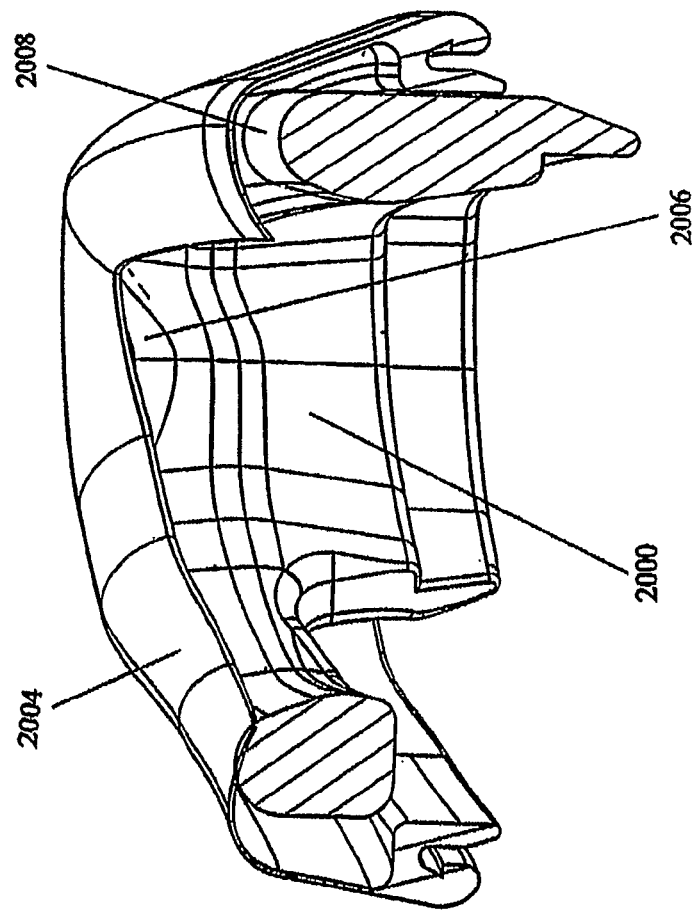
FIG. 8 shows a cross section of a second preferred embodiment of the sealing interface.
Figure 10:
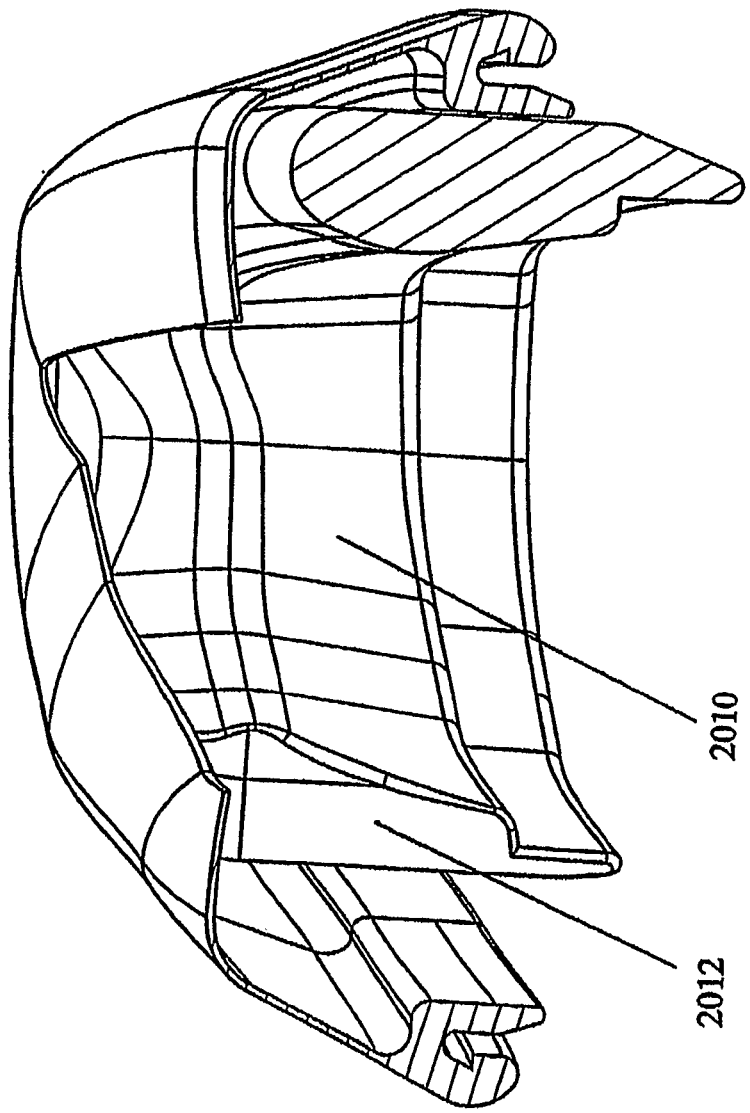
FIG. 10 shows a cross section of a third preferred embodiment of the inner and outer sealing members of the present invention.

A second preferred embodiment to the mask cushion is depicted in FIGS. 9 and 10. In the second embodiment the inner cushion 2000 includes a raised bridge 2002 in the nasal bridge region. The raised bridge 2002 can also be described as a cut out section made in the cushion. Also, the notch in the contacting portion (between the inner cushion and outer sheath) is less pronounced than proceeding embodiments. However, as the raised bridge 2002 is unsupported it is much more flexible and results in less pressure on the nasal bridge of the patient. The outer sheath 2004 contacts the inner cushion 2000 throughout the raised bridge 2002. The peaks 2005, 2007, 2009, 2011 in the inner cushion 2000 between each of the indented sections 2006, 2008 and the raised bridge 2002 contact the outer sheath 2004 and when in use the sheath 2004 contacts the facial contours of the patient in the regions of these peaks.

Referring particularly to FIG. 10 the inner cushion 2000 includes a cheek contour 2006 to follow the cartilage extending from the middle of the nose, and a contoured lip sealing portion 2008 to seal between the base of the nose and the upper lip.

Figure 12:
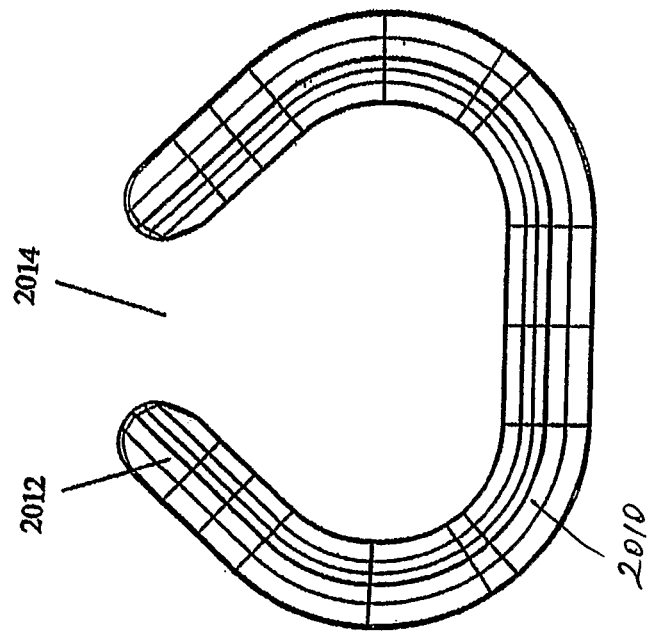
FIG. 12 shows a plan view of the inner sealing member of the third preferred embodiment of the mask cushion.
Figure 11:
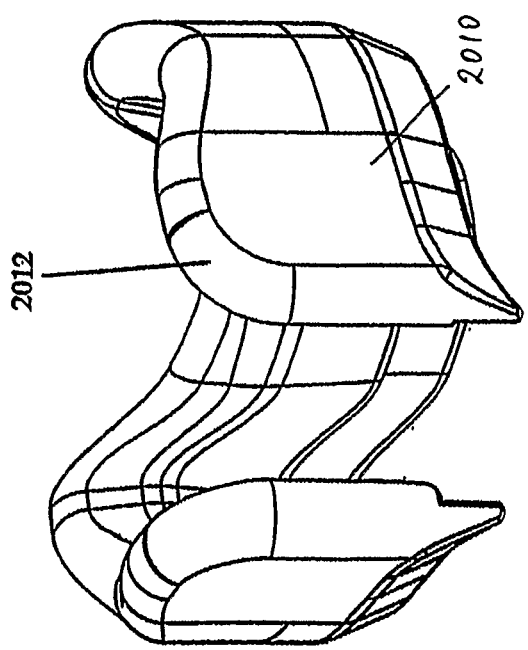
FIG. 11 shows a perspective view of the inner sealing member of the third preferred embodiment of the sealing interface.

Referring now to FIGS. 11 and 12 a third preferred embodiment of the mask cushion is depicted, in this case, the inner cushion 2010 tapers down 2012 towards the nasal bridge region 2014. For a short portion either side of the nasal bridge region 2014 the inner cushion 2010 is absent, forming a semi annular form in plan view as seen in FIG. 12.

Figure 13:
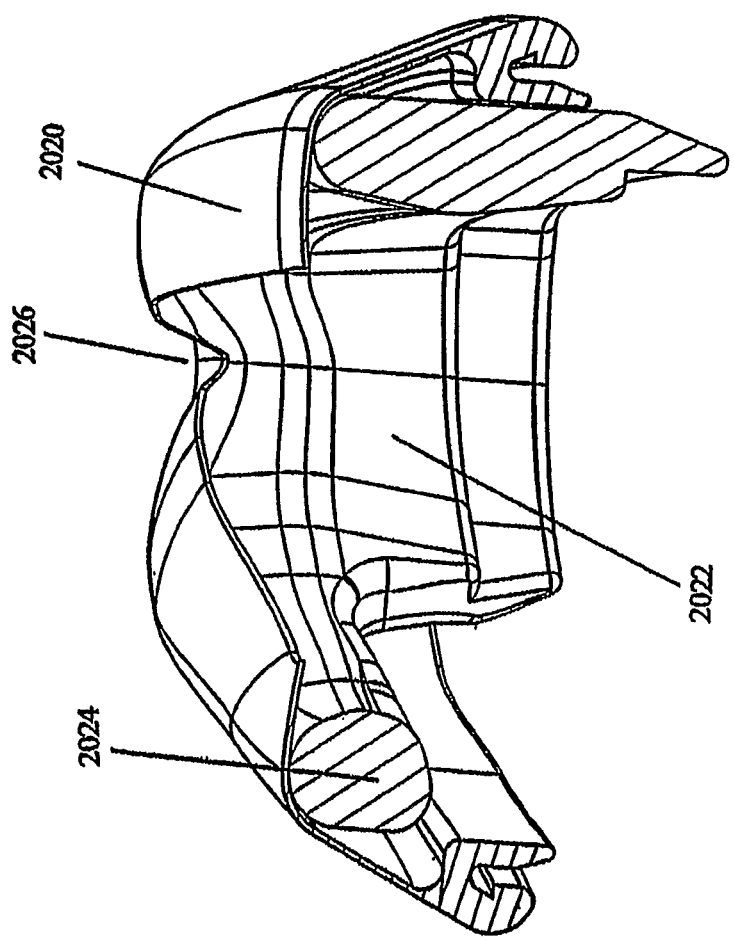
FIG. 13 shows a cross section of a fourth preferred embodiment of the sealing interface of the present invention.
Figure 18:
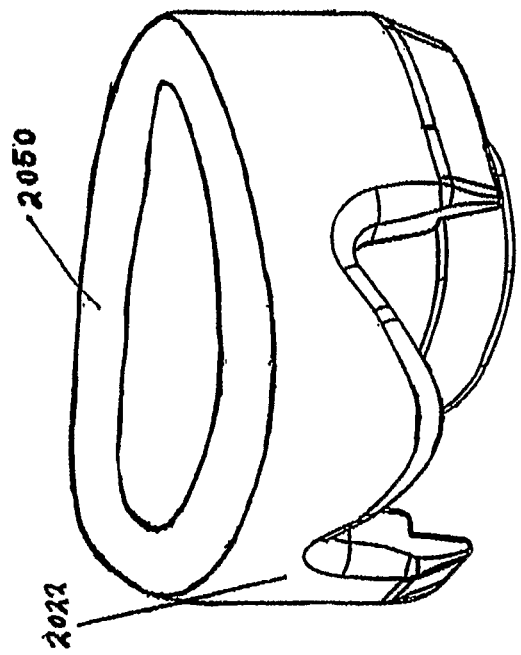
FIG. 18 shows a perspective view of the inner sealing member according to a ninth preferred embodiment of the sealing interface of the present invention.
Figure 20:
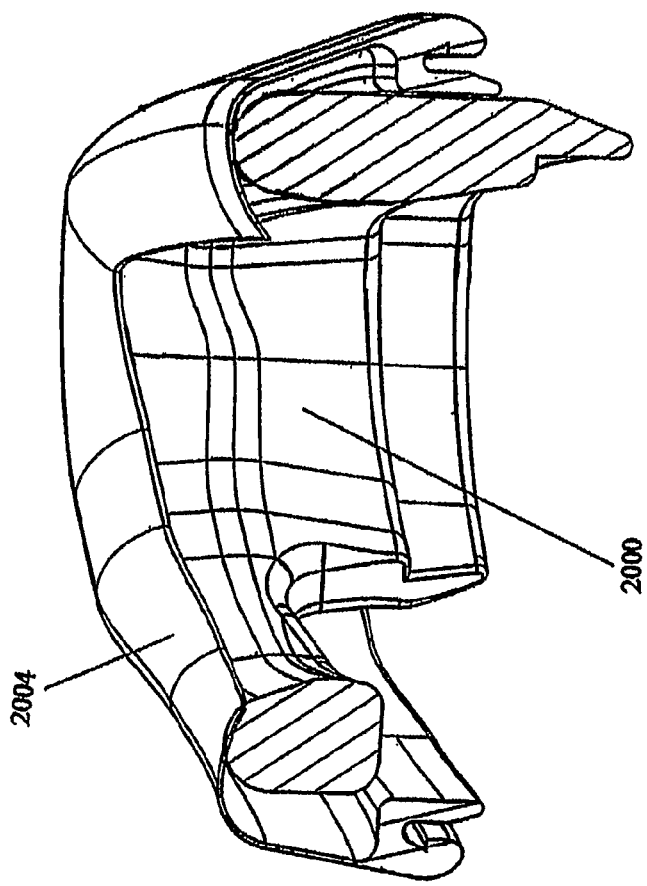
FIG. 20 shows a cross section of a further embodiment of the sealing interface of the present invention where the inner sealing foam member touches the outer sealing member at all times.

Referring to FIG. 13, a fourth preferred embodiment of the mask cushion is depicted. The outer sheath 2020 is adapted to contact the inner cushion 2022 completely about the inner cushion, including in the nasal bridge region 2024 and the check contour 2026. FIG. 18 shows the inner cushion 2022 where the upper edge 2050 of the cushion does not have any contours and thus will contact the outer sheath all around the edge of the inner cushion. FIG. 20 shows a sealing interface similar to that of FIG. 13 where the inner cushion also follows and touches the outer sheath all around its edge.

Figure 14:
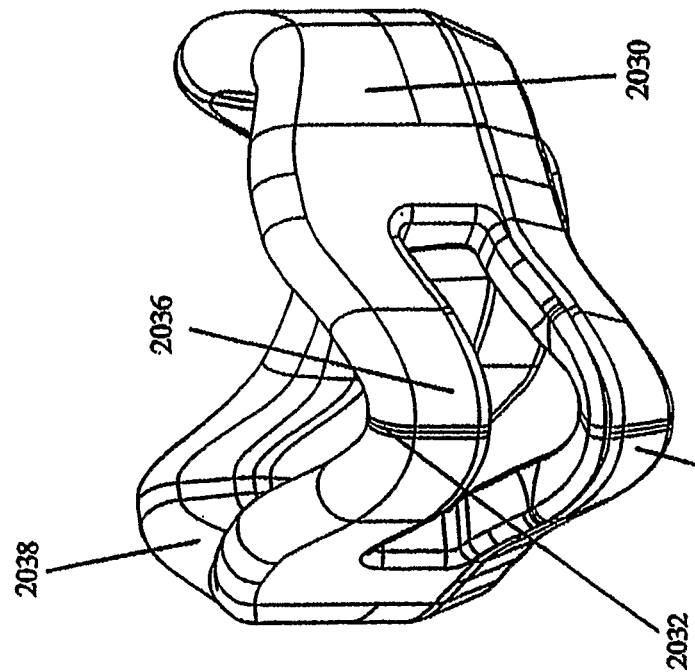
FIG. 14 shows a perspective view of the inner sealing member according to a fifth preferred embodiment of the sealing interface of the present invention.

FIG. 14 illustrates a fifth preferred embodiment of the inner cushion 2030. In the nasal bridge region 2032 the inner cushion includes a lower bridge 2034 and upper bridge 2036. Due to the gap the upper bridge 2036 is unsupported to reduce pressure on the patient's nasal bridge, but the lower rim 2034 of the inner cushion 2030 is continuous, which aids installation.

Figure 16:
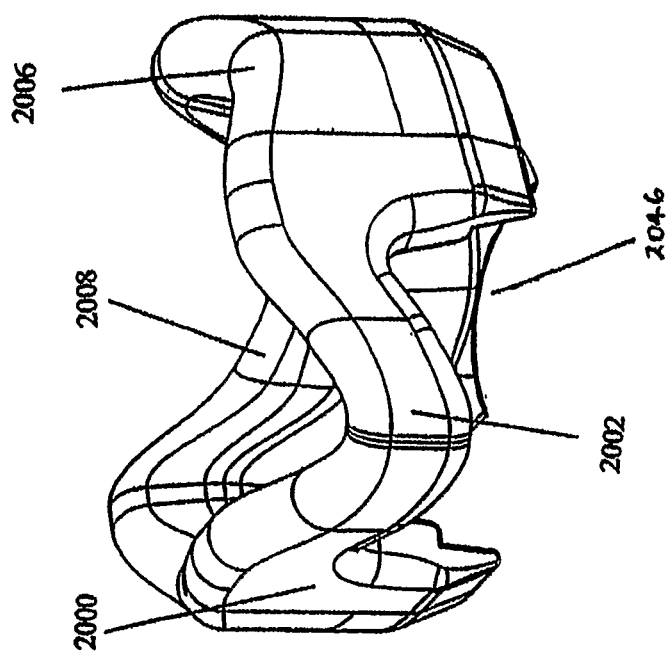
FIG. 16 shows a perspective view of the inner sealing member according to a seventh preferred embodiment of the sealing interface of the present invention.
Figure 15:
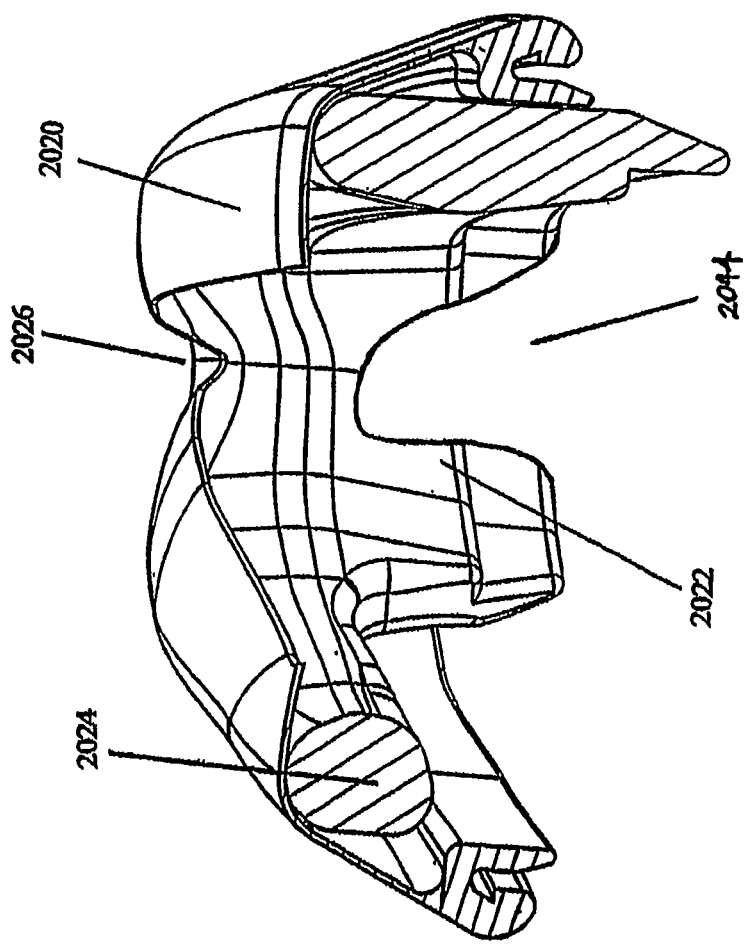
FIG. 15 shows a cross section of a sixth preferred embodiment of the sealing interface of the present invention.
Figure 17:
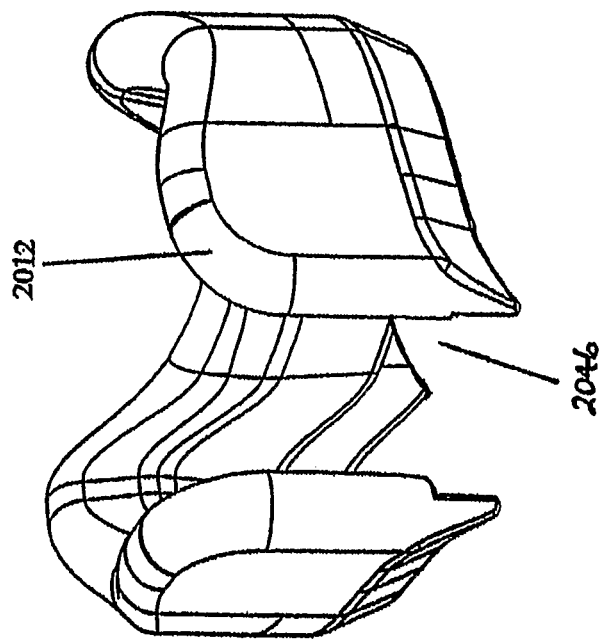
FIG. 17 shows a perspective view of the inner sealing member according to an eighth preferred embodiment of the sealing interface of the present invention.

In yet other forms of the sealing interface of the present invention the inner cushion may be provided with other contours on the front side of the inner cushion or cut outs on the back side of the inner cushion, so that in the areas where there are regions cut out of the back side of the cushion the cushion is more flexible. In particular, cut outs in the nasal bridge, cheek and upper lip regions provide the patient with a mask cushion that is more flexible and thus more comfortable. FIG. 15 shows an embodiment of an inner cushion 2024 that has a curved cut out or dead space 2044 in the cheek region. FIGS. 16 and 17 show embodiments of an inner cushion 2000 that has a cut out or dead space 2046 in the area where the patient's upper lip rests in the foam.

Figure 19:
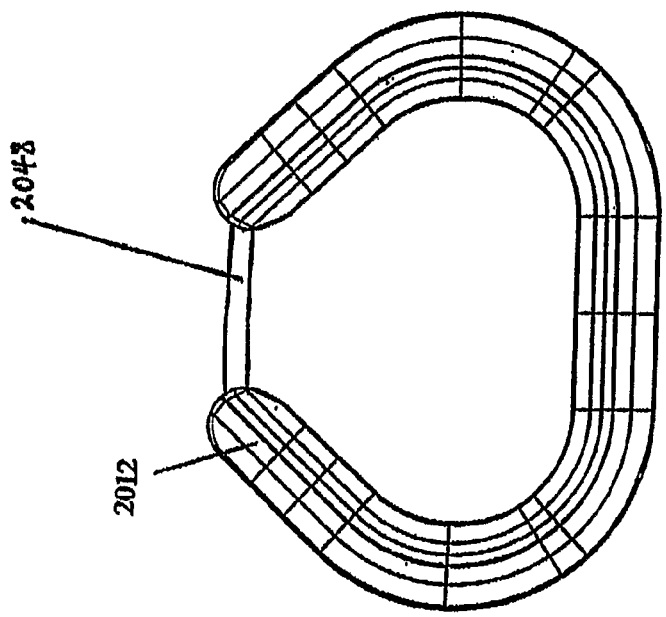
FIG. 19 shows a perspective view of the inner sealing member according to a tenth preferred embodiment of the sealing interface of the present invention.

A final form of a sealing interface is shown in FIG. 19, here the inner foam member has an annular shape but has a thin bridge or membrane 2048 that extends across and provides flexibility to the nasal bridge region.

Figure 21:
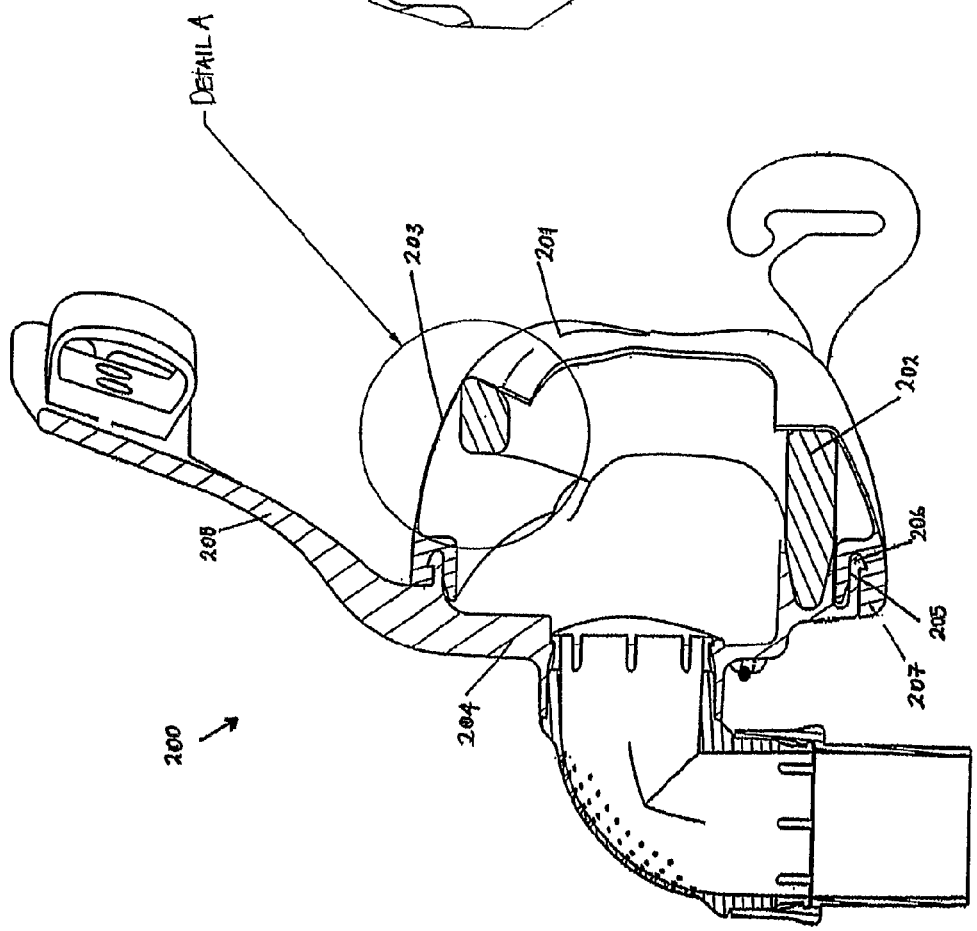
FIG. 21 is a side view of a nasal mask of the present invention where the outer sealing member is substantially thinner in width in the nasal bridge region than the rest of the outer sealing member.

Referring now to FIG. 21, to improve the comfort to the patient the nasal mask 200 includes a thin bridge section 203 in the nasal bridge region of the outer sealing member 201, that is, that part extending over the bridge of a patient's nose.

Similar to described above the outer sealing member or outer sheath 201 fits in place over the inner sealing member (inner cushion) 202, holding it in place. The outer sheath 201 is secured by a snap-fit to the periphery 205 of the mask hollow body 204. The periphery 205 is shown including an outer bead 206. The outer sheath 201 includes a matching bead 207, whereby once stretched around the periphery 205; the two beads engage to hold the outer sheath 201 in place.

Figure 22:
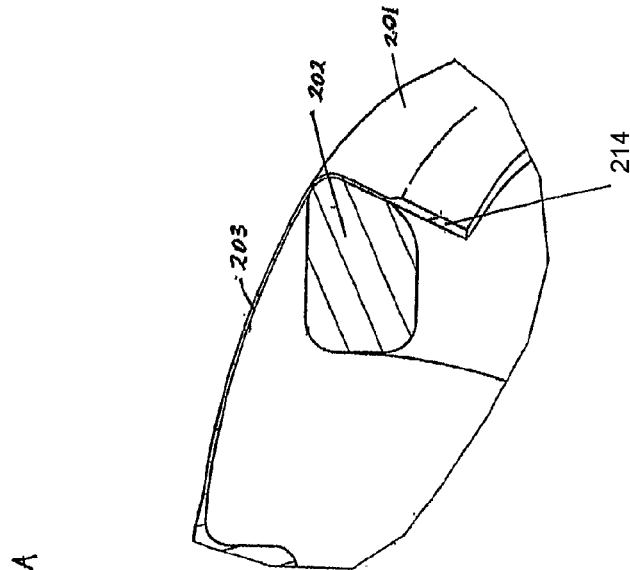
FIG. 22 is a close-up view of detail A in FIG. 21.
Figure 23:
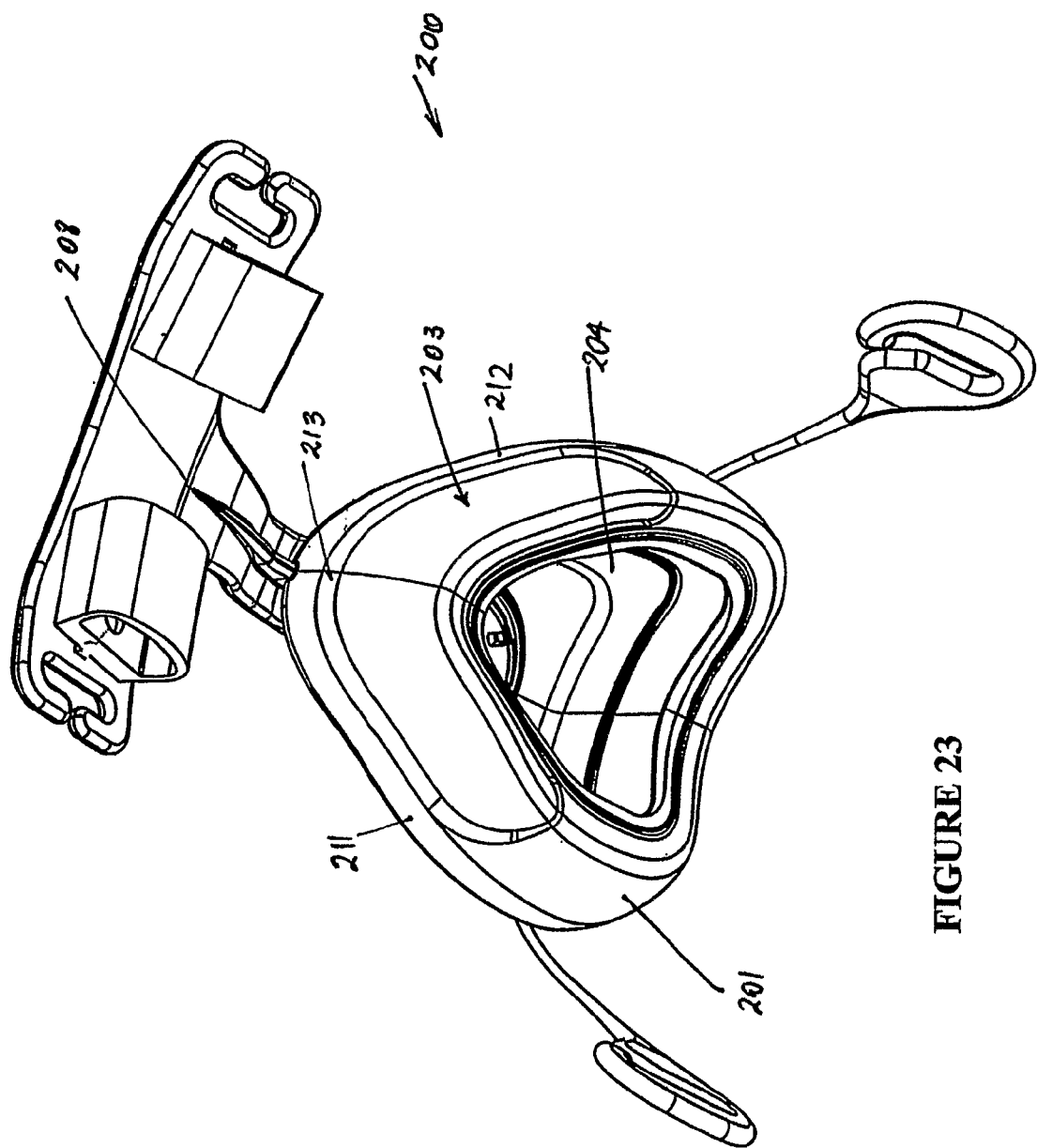
FIG. 23 is a perspective view of the nasal mask of FIG. 21.
Figure 24:
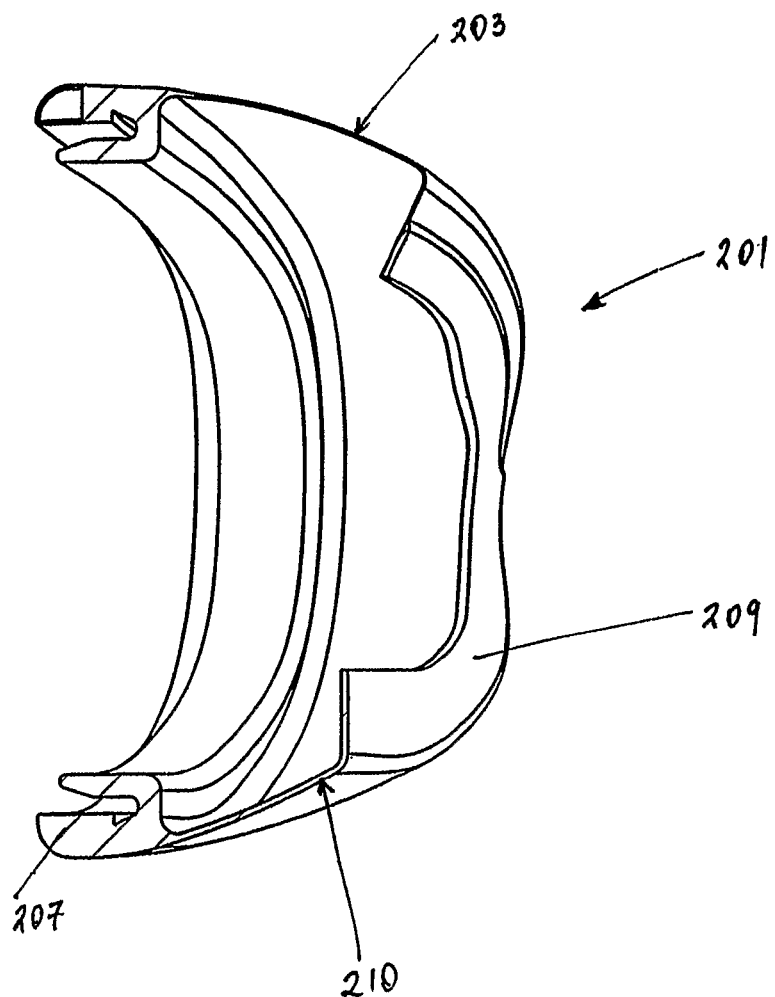
FIG. 24 is a cross-section of the outer sealing member of FIG. 21.

The outer sealing member or sheath 201 is shown in more detail in FIGS. 22 to 24. The outer sheath 201 has formed in it a region 203 that is thinner than the remainder of the cross-sectional thickness 210 of the sheath. In particular, the side walls 211, 212 (see FIG. 23) must be thicker than in the region 203 so as to provide structural support for the sheath and ensure the sheath does not collapse in use, or when being assembled with the mask body. As an example only, for a nasal mask, if the thin bridge region was 0.2 mm thick, the side walls may be 0.3 to 0.6 mm thick. Therefore, the thin bridge region 203 is approximately half the thickness of the rest of the sheath 201 and so can provide a significant effect, such that the pressure to the patient's nose in the nasal bridge region is reduced compared to when a sheath does not have any reduced thickness section. Furthermore, a thin bridge region 203 in the outer sheath 201 allows for different sized patient's to comfortably use the mask and outer sheath of the present invention.

In use, when a force is placed against the outer sheath 201 the thin bridge region 203 will collapse more than the rest of the outer sheath 201. Therefore, this section 203 is more flexible and allows for added patient comfort.

Referring particularly to FIG. 22, the thin bridge region 203 on the outer sheath 201 preferably does not extend completely to the outer edge 214 of the outer sheath 201, but grows thicker in thickness. This is because the outer edges of the outer sheath 201 when thicker are less prone to tearing.

In particular, in FIG. 23, that outer sheath 201 is substantially heart shaped and the thin bridge region 203 is shown to extend more than halfway down the sides of the sheath from the apex 213. As shown in FIG. 23, the thin bridge region 203 does not extend fully down the edges 211 and 212 of the outer sheath 201. This is because support is required in the edges of the sheath 201, to provide structural stability of the sheath.

Figure 30:
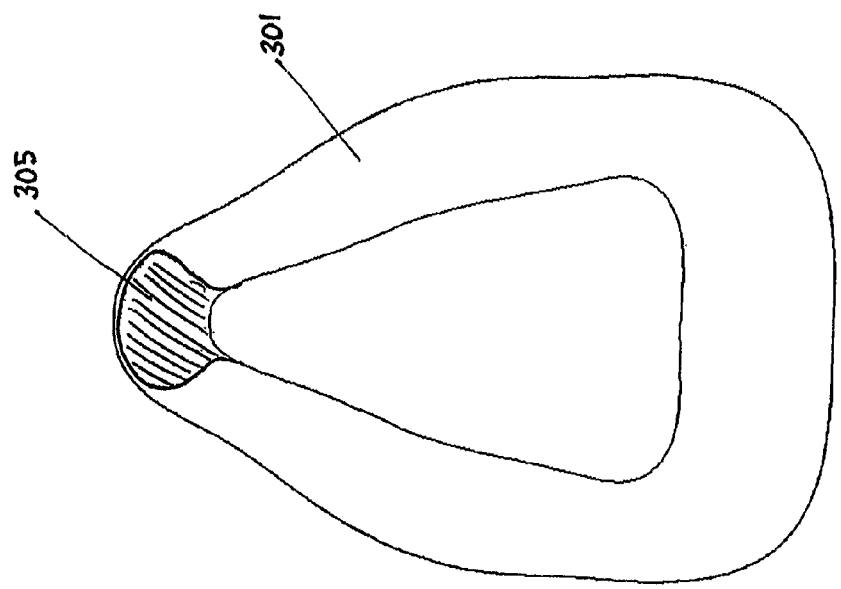
FIG. 30 is a front view of the outer sealing member of FIG. 28.

In other forms of the nasal mask of the present invention, the thin bridge region may not extend as far as that shown in FIG. 23, but be restricted merely to the nasal bridge region (similar in manner to the mask cushion shown in FIG. 30, in relation to a full face mask).

Full Face Mask

A further embodiment of the present invention is shown in FIGS. 25 to 31 where the patient interface is a full face mask similar to that described in co-pending New Zealand patent application number 528029. The full face mask 300 includes a hollow body 302 and outer sealing member or mask cushion 301. The cushion 301 is attached to the body 302 in a similar manner as described with reference to the nasal mask, but here no inner cushion is provided. Thus, the cushion 301 periphery extends over a flange on the mask body.

The hollow body 302 has an integrally formed recess (not shown) in which an insert 304 is fitted into. The recess and insert 304 each have complimentary circular apertures (generally indicated as 305) that form an inspiratory inlet when the insert 304 is placed in the recess. The inlet 304 is capable of being connected to the tubing that forms the inspiratory conduit 3 (as shown on FIG. 1). Gases, supplied to the inspiratory conduit 3 from the CPAP device and humidifier, enter the mask through the apertures 305 and the patient is able to breathe these gases. The mask 300 is positioned around the nose and mouth of the patient and headgear (not shown) may be secured around the back of the head of the patient to assist in the maintaining of the mask on the patient's face. The restraining force from the headgear on the hollow body 302 ensures enough compressive force on the mask cushion 301 to provide an effective seal against the patient's face.

The hollow body 302 and insert 304 are injection moulded in a relatively inflexible material, for example, polycarbonate plastic. Such a material would provide the requisite rigidity for the mask as well as being transparent and a relatively good insulator. The mask cushion 301 is preferably made of a soft plastics material, such as silicone, KRATON™ or similar materials.

Figure 29:
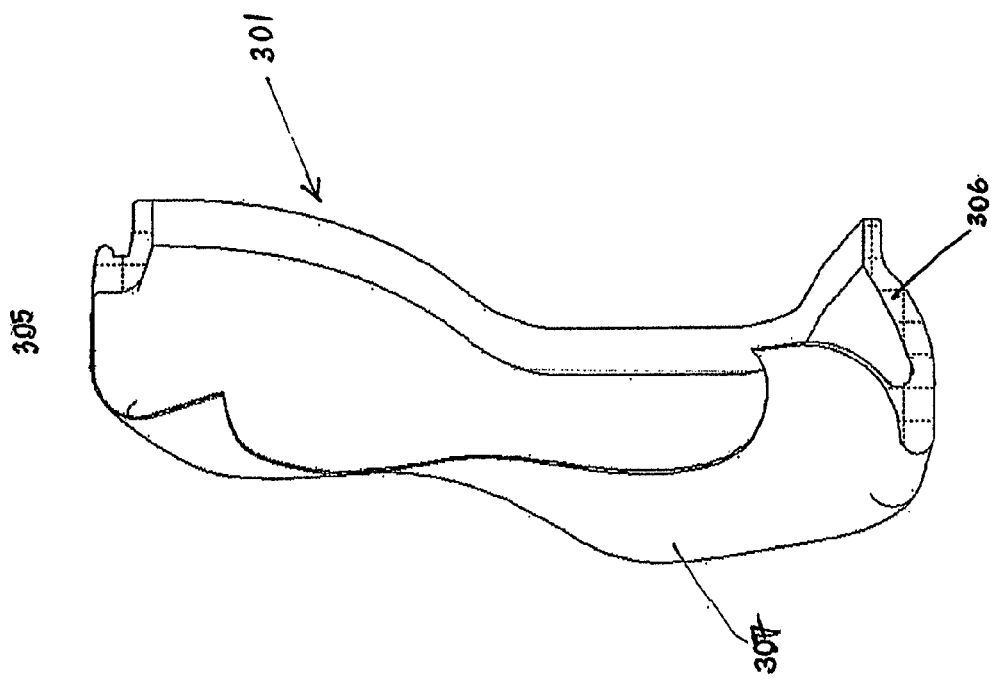
FIG. 29 is a cross-section through CC of the outer sealing member of FIG. 28.

The cushion 301 of the mask 300 includes a thin bridge section 305 in the nasal bridge region of the cushion 301, that is, that part extending over the bridge of a patient's nose. As an example, in the region of the thin bridge section 305 the walls of the cushion may be 0.2 to 0.3 mm thick and the rest of the cushion may have a thickness of 1 mm. In particular, the side walls need to be thicker to provide support in the cushion, so that it does not collapse during use or assembly with the mask body. In FIG. 29, this is particularly illustrated, as the section 305 in the nasal bridge region is shown as being much thinner than the rest of the cushion (in particular the bottom side wall region 306, which are much thicker in cross-section).

Note must be made that the inner flange 307 of the cushion 301 that rests against the patient's face is also thinner in section than the side walls of the cushion 301 to provide flexibility to the cushion and thus comfort to the patient. In use, the inner flange 307 is the area of the cushion that seals against the patient's face and the side walls of the cushion provide stability to the cushion 301.

In use, when a force is placed against the cushion 301 the thin bridge section 305 will collapse more than the rest of the cushion 301. Therefore, this section 305 is more flexible and allows for added patient comfort.

Other forms of the cushion that may be used with the fall face mask of the present invention are shown in FIGS. 31 to 33 and each show alternative thin sections that may be provided for patient comfort, and to allow for fitting to different sized patients.

Referring first to FIG. 31, cushion 310 may have a thin bridge section 311 that is narrower than that shown in FIG. 30.

In FIG. 32 the cushion 312 has a thin bridge section 313 only near the outer edge 317 of the cushion 312. This cushion 312 also had a thin section 314 in the region of the cushion that would rest against the patient's chin.

Finally, in FIG. 33, the thin section 316 of the cushion 315 may extend down the sides 318, 319 of the cushion.

Forehead Rest

Figure 25:
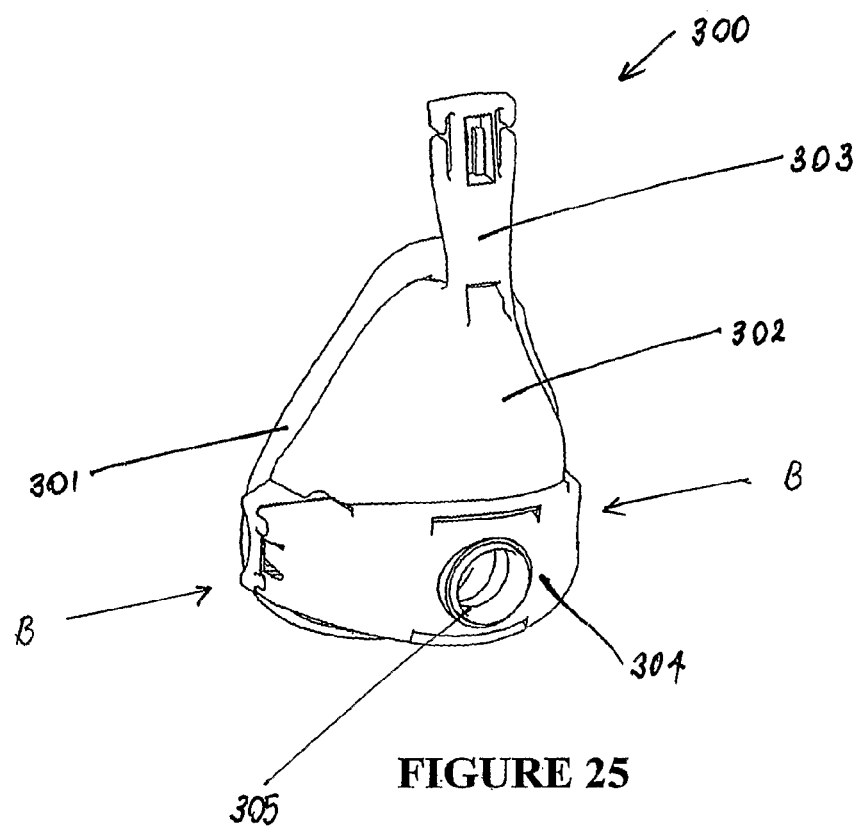
FIG. 25 is a front perspective view of a full face mask of the present invention, where the outer sealing member is substantially thinner in width in the nasal bridge region than the rest of the outer sealing member.
Figure 26:
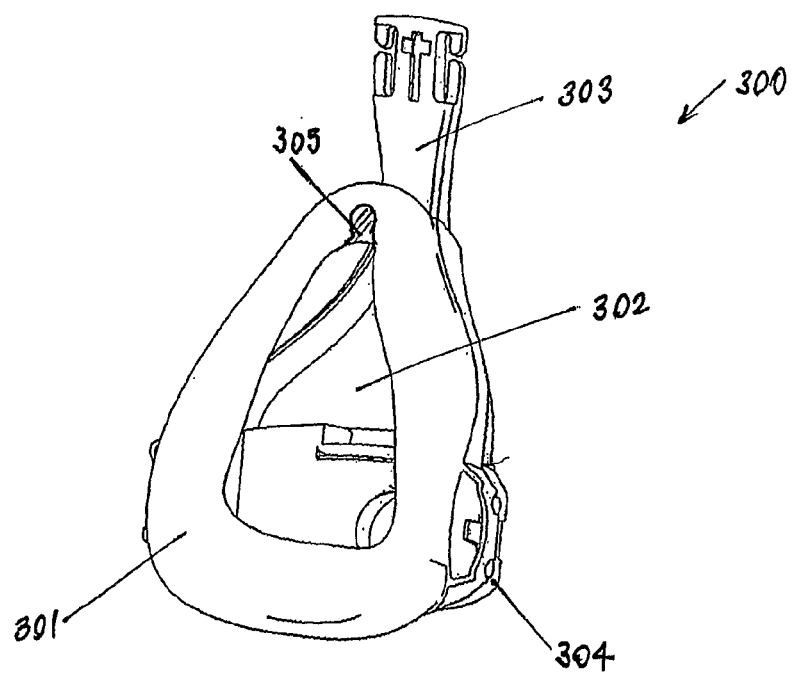
FIG. 26 is a back perspective view of a full face mask of FIG. 25.
Figure 27:
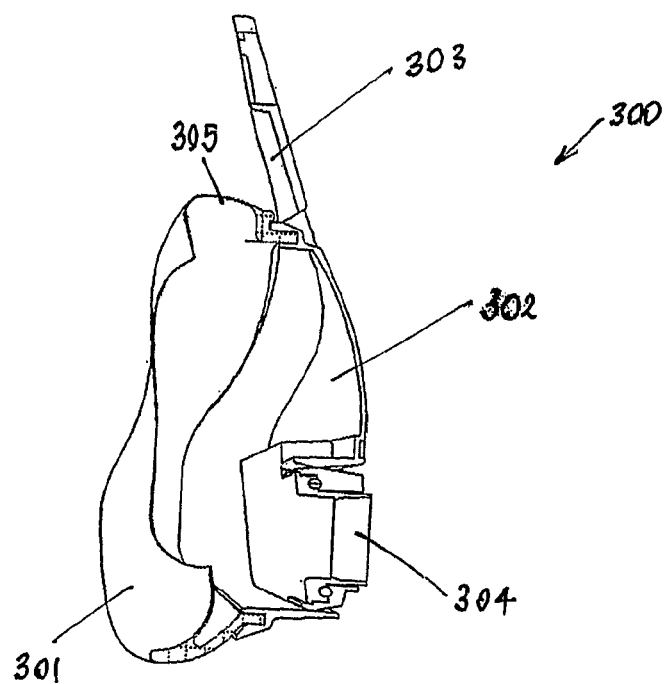
FIG. 27 is a cross-section through BB of the full face mask of FIG. 25.
Figure 28:
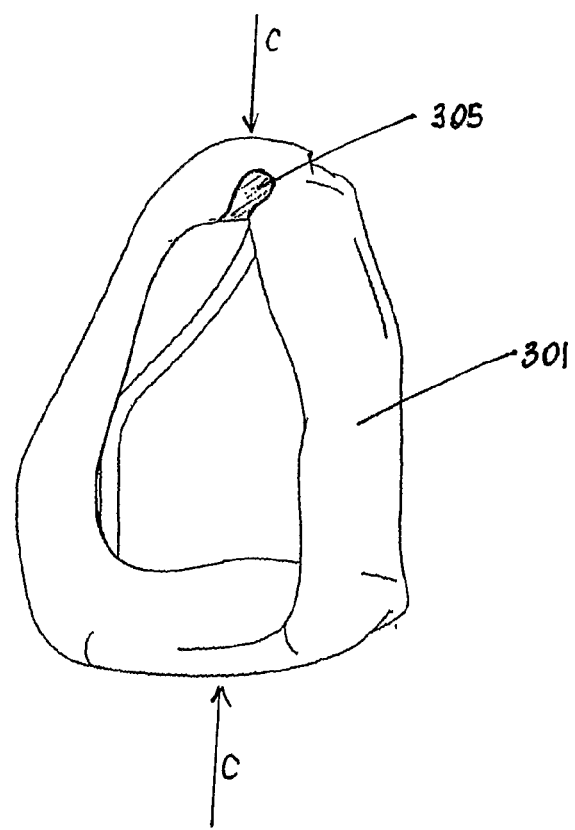
FIG. 28 is a perspective view of the outer sealing member of the fall face mask of FIG. 25 in isolation, where the thin nasal bridge region is particularly shown.

The nasal mask and/or fall face mask of the present invention is preferably provided with a fixed forehead rest (208, as shown in relation to the nasal mask in FIGS. 21 and 23 or 303, as shown in relation to the full face mask in FIG. 25). The forehead rest is not required to be adjustable as the cut out in the nasal bridge region of the inner foam (for the nasal mask) and the thin section in the outer sheath (for both the nasal and full face masks) provides enough flexibility of the mask cushion to provide fitting to a number of different patients.

We claim:

1. A breathing assistance apparatus comprising:
   a mask body adapted to cover the nose, or nose and mouth, of a patient, and
   a sealing interface including at least an outer sealing member arranged about an opening in said mask body, said outer sealing member being adapted to seal around a patient's facial contours,
   said outer sealing member being a single wall membrane, the single wall membrane including:
      an outer peripheral wall portion having a mask flange adapted to attach to said mask body, and
      an inner sealing flange provided about a patient end of said peripheral wall portion, and
      a face contacting portion that joins said outer peripheral wall portion and said inner sealing flange and is configured to contact a patient's face in use,
      said outer sealing member having a thin region and a thick region, said thin region being located in a nasal bridge region configured to extend over and contact a patient's nasal bridge in use said thin region comprising portions of each of said inner sealing flange and said face contacting portion, and said thin region extending downward from an apex of said outer sealing member and ending in cheek regions of said outer sealing member, and
      said thick region comprising a remainder of said face contacting portion, a portion of said outer peripheral wall and an inner edge of said inner sealing flange extending along an entire inner perimeter of said outer sealing member.

2. A breathing assistance apparatus according to claim 1 wherein sidewalls of said peripheral wall portion of said outer sealing member are at least twice the cross-sectional thickness of said bridge region.

3. A breathing assistance apparatus according to claim 1 wherein said sealing interface is a full face mask.

4. A breathing assistance apparatus according to claim 1 wherein said sealing interface is a nasal mask.

5. A breathing assistance apparatus according to claim 1 wherein said sealing interface includes an inner cushion, wherein said inner cushion is separate from said outer sealing member and has a raised section in said bridge region.

6. A breathing assistance apparatus according to claim 5 wherein said inner cushion and said outer sealing member are continuously in contact.

7. A breathing assistance apparatus according to claim 6 wherein said inner cushion includes a contoured region that is configured to be positioned adjacent a patient's cheeks in use, said contoured region is concave so as to accommodate cartilage extending away from the nose of a patient.

8. A breathing assistance apparatus according to claim 6 wherein said bridge region of said peripheral wall portion tapers away from said patient with respect to the reminder of said peripheral wall portion.

9. A breathing assistance apparatus according to claim 1, said contacting portion shaped to approximately follow the contours of a patient's face.

10. A breathing assistance apparatus according to claim 9 wherein said contacting portion is a peripheral ridge,
wherein said sealing flange extends inwardly from said peripheral ridge, said sealing flange configured to seal said breathing assistance apparatus against a patient's face.

11. A breathing assistance apparatus according to claim 10 wherein said sealing flange is shaped to follow the contours of said peripheral ridge.

12. A breathing assistance apparatus according to claim 9 wherein said breathing assistance apparatus further comprises an inner cushion arranged about said opening in said mask and adjacent said outer sealing member, said inner cushion in continuous contact with said outer sealing member at said contacting portion.

13. A user interface comprising:
a mask body, and
a resilient sealing member arranged about an opening in the mask body, the sealing member being a single wall membrane having a mask end and a user end, the mask end connecting to the mask body about the opening and the user end being spaced from the mask body and configured to rest adjacent a user's face,
the sealing member further comprising a peripheral wall portion that extends from the mask end to the user end, the peripheral wall portion including a thin bridge region that is adapted to be positioned adjacent and is configured to contact a user's nasal bridge in use, wherein the thin bridge region is positioned between and has a smaller cross-sectional thickness than the mask end and the user end of the sealing member such that the sealing member's cross-sectional thickness is greater at the mask end and user end than at the thin bridge region, and wherein the thin bridge region ends in cheek regions of the sealing member such that the thin bridge region has a smaller cross-sectional thickness than laterally adjacent regions of the peripheral wall portion configured to contact an upper lip or chin of the user's face in use.

14. A user interface according to claim 13 wherein a material thickness of the bridge region is significantly less than a material thickness of adjacent portions of the peripheral wall portion.

15. A user interface according to claim 13 wherein a material thickness of the bridge region is significantly less than a material thickness of a remainder of the peripheral wall portion.

16. A user interface according to claim 15 wherein the contacting portion and the sealing flange are shaped approximately to a user's facial contours.

17. A user interface according to claim 13 wherein the resilient sealing member further comprises a contacting portion configured to contact a user's face, the contacting portion positioned between said peripheral wall portion and said user end.

18. A user interface according to claim 17 wherein the resilient sealing member further comprises a sealing flange configured to form a seal with a user's face, the sealing flange extending inwardly from the contacting portion.

19. A user interface according to claim 13 wherein the peripheral wall portion has a flattened base securing portion configured engage with a complimentary securing track arranged about the opening in the mask body to secure the sealing member in place.

20. A sealing member for a user interface comprising:
a peripheral wall having an outer surface and an innermost surface, the outer and innermost surfaces being formed of a single wall membrane arranged in a loop and configured to enclose a user's nose or nose and mouth, the peripheral wall having a mask end configured to engage with a respiratory mask and a user end configured to contact a user's face, and
a sealing flange arranged about the user end of the peripheral wall and projecting inwardly of the closed loop and terminating in a suspended end, the flange configured to seal against a user's face,
wherein the peripheral wall includes a bridge region that is adapted to be positioned adjacent and is configured to contact a user's nasal bridge in use, the bridge region having a reduced cross-sectional thickness compared to the mask end of the peripheral wall and the suspended end of the sealing flange, the bridge region extending downward from an apex of the peripheral wall and ending in cheek regions of said peripheral wall.

21. A sealing member according to claim 20 wherein a material thickness of the bridge region is significantly less than a material thickness of adjacent portions of the peripheral wall.

22. A sealing member according to claim 20 wherein a material thickness of the bridge region is significantly less than a material thickness of the remainder of the peripheral wall.

23. A sealing member according to claim 20 wherein a contacting ridge is formed at an interface between the peripheral wall and the sealing flange, the contacting ridge being shaped approximately to the contours of a user's face.

24. A breathing assistance apparatus comprising:
a mask body adapted to cover a nose, or nose and mouth, of a patient, and
a sealing interface including at least an outer sheath, said outer sheath being adapted to contact facial contours of the patient and being a single wall membrane having an upper apical portion,
said outer sheath comprising a mask flange configured to removably engage an edge of said mask body, said outer sheath comprising a side wall that extends away from said mask flange and that defines a periphery of said outer sheath, said outer sheath comprising a lip, said lip defining an opening adapted to receive the nose, or nose and mouth, of the patient, said opening having an uppermost extent,
said outer sheath having a thin region, said thin region being positioned in said upper apical portion, said thin region extending downward beyond said uppermost extent of said opening, said thin region being disposed between said lip and said mask flange, said thin region ending in cheek regions of said outer sheath such that at least a portion of said sidewall is also positioned between said thin region and said mask flange, and said thin region having a smaller thickness than said mask flange, said sidewall and said lip.

25. The breathing assistance apparatus of claim 24, wherein said thin region defines a majority of a surface area of said upper apical portion.

26. The breathing assistance apparatus of claim 24, wherein said thin region extends more than halfway down a total height of said outer sheath.

27. The breathing assistance apparatus of claim 24, wherein said upper apical portion includes a bridge region that extends over a nasal bridge of the patient in use.

\* \* \* \* \*